Oct. 27, 1953 E. S. BOERNER Plant Pat. 1,225
ROSE PLANT
Filed Oct. 9, 1952
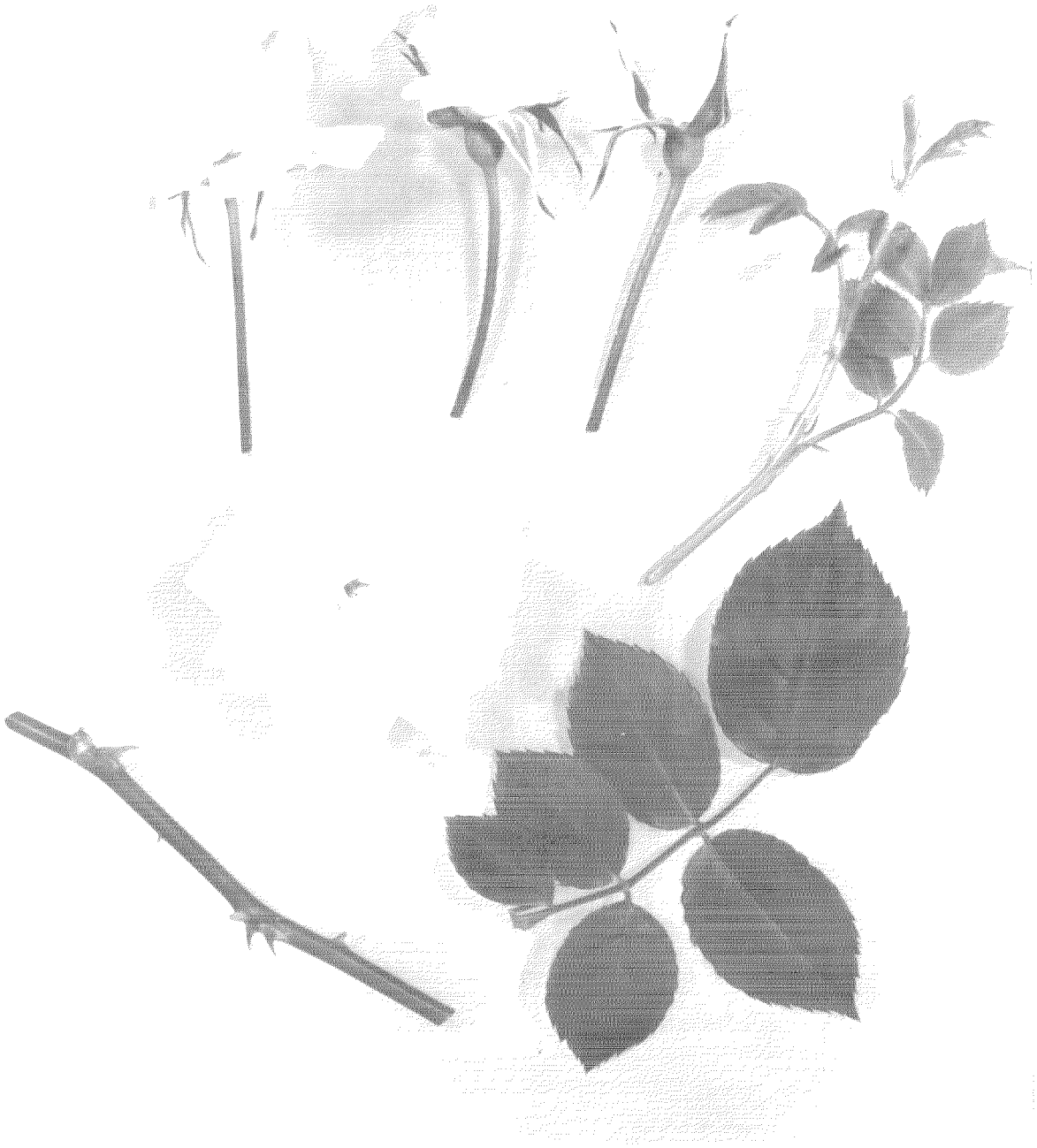
Inventor.
E. S. Boerner
By: Robb & Robb
attorneys Patented Oct. 27, 1953

Plant Pat. 1,225

UNITED STATES PATENT OFFICE 1,225

ROSE PLANT

Eugene S. Boerner, Newark, N. Y., assignor to Jackson & Perkins Company, Newark, N. Y., a corporation of New York Application October 9, 1952, Serial No. 313,997

1 Claim. (Cl. 47—61)

The present invention relates to a new and distinct variety of rose plant of the large-flowered polyantha class, which was originated by me by crossing an unnamed and unpatented white seedling of "Pinocchio" (Plant Patent No. 484) with the variety "Garnette" (unpatented).

The objective in making this cross was to produce and obtain a white-colored rose comparable in form to the red flowers of "Garnette." This objective was fully attained, together with additional improvements, as evidenced by the fact that my new variety is endowed with the following outstanding and distinctive characteristics which distinguish it from its parents, as well as from all other varieties of its class:

(1) The extremely bushy habit of growth of the plants;

(2) The great number of flowering clusters which are produced on the plants and which make it particularly useful for the florist industry;

(3) The white general color tonality of the flowers which have a form comparable to those of "Garnette," with relatively thin petals; and (4) The long-lasting quality of the flowers when used as cut-flowers.

Asexual reproduction of my new variety by budding at Newark, New York, and at Pleasanton, California, shows that the foregoing characteristics and distinctions come true to form and are established and transmitted through succeeding propagations.

The accompanying drawing shows specimens of the flowers, stems and foliage of my new variety, with the flowers and foliage in different stages of development.

The following is a detailed description of my new variety, with color terminology in accordance with Ridgway's Color Standards and Nomenclature:

Parentage: Seedling.

*Seed parent.*—An unnamed white seedling of "Pinocchio."

*Pollen parent.*—"Garnette."

Classification:

*Botanic.*—Large-flowered polyantha.

*Commercial.*—Floribunda.

*Flower*

(Observations made in a greenhouse at Newark, New York, in the late morning early in the month of May.)

Blooming habit: Recurrent—continuous.

Bud:

*Size.*—Small.

*Form.*—Ovoid; is not affected by wet or hot weather.

*Color.*—When sepals first divide—Sea-foam Yellow, Plate 31. When petals begin to unfurl—White, Plate 53, lightly overcast with Sea-foam Yellow, Plate 31. When half blown: inside of petals—White, Plate 53; reverse of petals—White, Plate 53, lightly overcast with Sea-foam Yellow, Plate 31.

*Sepals.*—Slightly branched; "hood" above bud; curl back when petals begin to unfurl. Color: inside—Light Elm Green, Plate 17; outside—Cress Green, Plate 31.

*Calyx.*—Color—Absinthe Green, Plate 31. Shape—Apple. Size—small. Aspect—smooth. Odor when rubbed—none.

*Peduncle.*—Length—short. Aspect—rough. Color—Cress Green, Plate 31. Strength—bending; slender.

*Opening.*—Opens up well; is not affected by adverse weather conditions.

Bloom:

*Size.*—Small; average size when fully expanded—1½ inches to 2 inches.

*Borne.*—Several together and in flat clusters.

*Stems.*—Medium length; normal strength.

*Form.*—When first open—cupped. Permanence—flattens.

*Petalage.*—Double (full but open center). Number of petals under normal conditions—30 to 35.

*Color.*—Center of flower—White, Plate 53. Outer petals—White, Plate 53, lightly overcast with Sea-foam Yellow, Plate 31. Base of petals (aiglet)—Citron Yellow, Plate 16. Inside of petals—White, Plate 53. Reverse of petals—White, Plate 53, lightly overcast with Sea-foam Yellow, Plate 31. General tonality from a distance—White, Plate 53.

*Discoloration.*—General tonality at end of first day—White, Plate 53, lightly overcast with Sea-foam Yellow, Plate 31. Second day—White, Plate 53. Third day—White, Plate 53.

Petals:

*Texture.*—Thin; is not affected by wet or hot weather.

*Appearance.*—Inside—satiny; outside—shiny.

*Form.*—Oval.

*Arrangement.*—Imbricated (regularly arranged shingle-like).

*Petaloids in center.*—Few; small.

*Persistence.*—Drop off cleanly.
*Fragrance.*—Slight. Nature—tea (average hybrid tea scent).
*Lasting quality.*—On the plant and as cut-flower—very long.

*Genital organs*

Stamens, anthers: Small; few.
*Color.*—Sea-foam Yellow, Plate 31.
*Arrangement.*—Regular around styles.
Stamens, filaments (threads): Short. Color—Pale Chalcedony Yellow, Plate 17.
Pollen: Color—Lemon Chrome, Plate 4.
Styles: Bunched; uneven length; short; thin.
Stigmas: Color—Sulphur Yellow, Plate 5.
Ovaries: All enclosed in calyx.
Seeds: None.

*Plant*

Form: Bush.
Growth: Vigorous; branching.
Foliage: 5 to 7 leaflets.
*Size.*—Medium.
*Quantity.*—Abundant.
*Color.*—New foliage: upper side—Oil Green, Plate 5; serrations Oxblood Red, Plate 1; under side—Yellowish Oil Green, Plate 5, overcast with Oxblood Red, Plate 1. Old foliage: upper side—Elm Green, Plate 17; under side—Light Elm Green, Plate 17.
*Shape.*—Oval pointed.
*Texture.*—Upper side—leathery; under side—smooth. Ribs and veins—ordinary.
*Edge.*—Serrated (saw-toothed).
*Serration.*—Single; sharp.

*Leaf stem.*—Color—Grass Green, Plate 6. Under side—prickles.
*Stipules.*—Medium length; bearded.
Wood:
*New wood.*—Color—Parrot Green, Plate 6, lightly overcast with Oxblood Red, Plate 1. Bark—smooth.
*Old wood.*—Color—Cress Green, Plate 31. Bark—smooth.
Thorns:
*Thorns.*—Quantity: On main stalks from base—ordinary; on laterals from stalk—few. Form—narrow base; medium length; hooked downward. Color when young—Eugenia Red, Plate 13. Position—irregular.
*Prickles.*—Quantity—on main stalks—few. Color—Citrine, Plate 4.
*Short needles.*—Quantity—on main stalks and on laterals—none.

I claim:

A new and distinct variety of rose plant of the large-flowered polyantha class, substantially as herein shown and described, characterized particularly as to novelty by its bushy habit of growth, by its great number and constant production of flowering clusters, by the white general color tonality of its flowers of a form comparable to those of "Garnette" (unpatented), by the relatively thin petals of its flowers, and by the long-lasting quality of its flowers when cut.

EUGENE S. BOERNER.

No references cited.